United States Patent [19]

Ferrari et al.

[11] 4,176,182
[45] Nov. 27, 1979

[54] SULFAMOYL DERIVATIVES OF 8-β-AMINOMETHYLERGOLINE

[75] Inventors: Giorgio Ferrari; Vittorio Vecchietti, both of Milan, Italy

[73] Assignee: SIMES Societa Italiana Medicinali e Sintetici S.p.A., Milan, Italy

[21] Appl. No.: 848,530

[22] Filed: Nov. 3, 1977

[30] Foreign Application Priority Data

Nov. 24, 1976 [IT] Italy .............................. 29704 A/76

[51] Int. Cl.$^2$ .................. C07D 457/02; A61K 31/48
[52] U.S. Cl. ................................ 424/248.5; 424/250; 424/261; 544/125; 544/361; 546/67; 260/244.4
[58] Field of Search .................... 260/285.5; 424/261, 424/248.5, 250; 544/125, 361

[56] References Cited

U.S. PATENT DOCUMENTS

| | | | |
|---|---|---|---|
| 3,228,944 | 1/1966 | Bernardi et al. | 544/125 |
| 3,238,211 | 3/1966 | Camerino et al. | 260/285.5 |
| 3,557,118 | 1/1971 | Arcamone et al. | 260/285.5 |
| 3,646,046 | 2/1972 | Arcamone et al. | 544/125 |

OTHER PUBLICATIONS

Morrison et al.; Organic Chemistry, pp. 751–753, (1969).
Magnus, Pfluger Arch. ges, Physiol, 102, pp. 123–151, (1904).
Fehr et al.; Eur. J. Med. Chem., 9, pp. 597–601, (1974).
Hofmann, "Die Mutterkornalkaloide", F. Enke, Stuttgart, pp. 176–197, (1964).
Brugger, Helv. Physiol, Pharm. Acta, vol. 3, pp. 117–134, (1945).
Erspamer, Archiv. Int. Pharmacodyn., 93, pp. 293–316, (1953).
Corne et al., Brit. J. Pharm., 20, pp. 106–120, (1963).
Luduena et al.; Archiv. Int. Pharm., 122, pp. 111–122, (1955).
Bernardi et al., Gazz Chim. It., 94, pp. 936–946, (1964).

*Primary Examiner*—Donald G. Daus
*Assistant Examiner*—M. Lee

*Attorney, Agent, or Firm*—Cushman, Darby & Cushman

[57] ABSTRACT

Novel sulfamoyl derivatives of 8β-aminomethyl ergoline having the general formula:

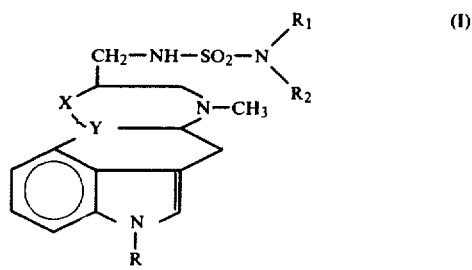

are disclosed, which have interesting pharmacological properties and are useful as anti-migrainic, anti-hypertensive and psychopharmaceutically active drugs. In the method for their preparation a compound having the formula:

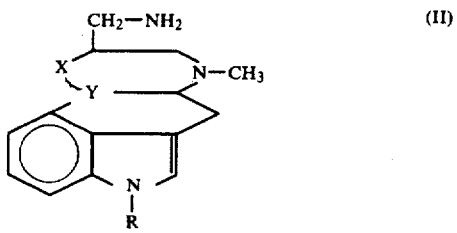

is reacted, in an aprotic solvent and at a temperature of between −20° C. and +150° C., with a compound having the formula:

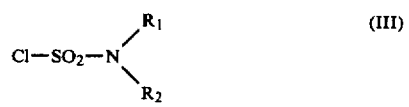

18 Claims, No Drawings

SULFAMOYL DERIVATIVES OF 8-β-AMINOMETHYLERGOLINE

The present invention relates to the preparation and the use of novel ergoline derivatives having the following general formula (I):

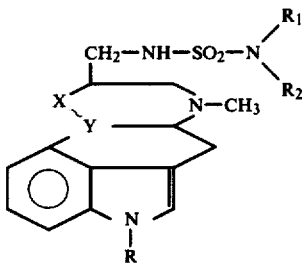

wherein x∼y is CH=C< or CH$_2$—CH<.

R is hydrogen, C$_1$-C$_3$ alkyl, C$_3$-C$_5$ alkylene, C$_3$-C$_4$ alkyne radicals R$_1$=R$_2$ represent C$_1$-C$_3$ alkyl, R$_1$ and R$_2$ being optionally connected to each other to form rings with C$_1$-C$_8$ members (e.g. pyrrolidine) or connected to form a ring possibly containing a heteroatom, like nitrogen or oxygen, whereby a heterocyclic compound is formed, such as for instance piperazine, morpholine.

The term alkyl indicates a group such as methyl, ethyl, isopropyl; the term alkylene indicates a group such as allyl, crotyl; and the term alkyne indicates a group like propargyl, butynyl.

It has been found that the compounds having general formula (I) can be preparing by reacting the compounds having general formula (II):

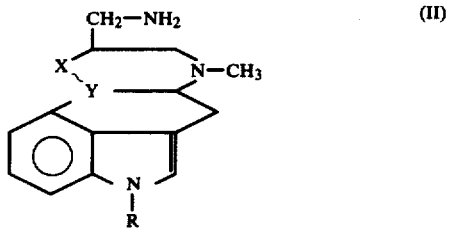

wherein x∼y and R have the above meanings with compounds having general formula III:

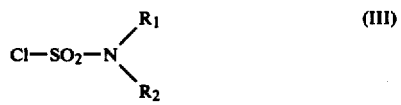

in which R$_1$ and R$_2$ also have the above defined meanings, in an aprotic solvent, such as acetone, tetrahydrofurane, dioxane, dimethylformamide, dimethylsulfoxide, hexamethylenphosphoric-triamide, etc., in the presence of inorganic bases, like NaHCO$_3$, Na$_2$CO$_3$ or organic bases such as triethylamine, diisopropylethylamine, piridine, quinoline, etc. at a temperature of between −20° C. and +150° C.

The reaction products are isolated by the standard methods of the preparation chemistry and purified through crystallization or chromatography; preferably carried out on SiO$_2$.

The compounds of the present invention are solids, almost always crystalline, and form pharmaceutically acceptable salts with nontoxic, organic or inorganic, acids, which can be formulated into pharmaceutical compositions for oral or parenteral use.

The non toxic acids used for the preparation of the salts include mineral acids, such as hydrogen chloride and bromide, sulfuric acid, phosphoric acid, etc., and organic acids, such as methansulfonic, citric, tartaric, maleic, fumaric, succinic acids, etc.

It has been found that the novel compounds of the present invention possess interesting pharmacological properties. More specifically, these compounds are powerful and selective anti-serotonin agents and the foreseen therapeutical use thereof is as anti-migrainic, anti-hypertensive and psychopharmaceutically active drugs.

These novel compounds show anti-serotonin activity both peripherally and on the central nervous system. This activity had been tested "in vitro" through the inhibition of the contractions as induced by 5-hydroxytryptamine (serotonin) (5 HT) in the uterus of a female rat, which 20 hours before the test had been treated with estradiol dipropionate (see Ersparmer, Archiv. int. Pharmacodyn. 93, 293, 1953), and "in vivo" on the clones induced by tryptamine (40 mg/kg i.v.) in the rat (S. J. Corne et al., Brit. J. Pharmacol., 20, 106, 1963).

The adrenolytic activity (J. Brügger, Helv. Physiol. Pharm. Acta 3, 117, 1945, and F. P. Luduena et al, Archiv. int. Pharmacodyn., 122, 111, 1955) and the spasmolytic activity (Magnus, Pflüger Arch. ges. Physiol., 102, 123, 1904) typical of the ergolinic derivatives (A. Hofmann, "Die Mutterkornalkaloide", F. Enke Verlag/Stuttgart, 1964), as shown "in vitro" by these novel substances are revealed at concentrations remarkably higher than those by which 5 HT is inhibited.

In the following TABLE the data relating to the novel compounds are reported in comparison with the substances selected as the comparison compounds, namely methergoline as anti-5 HT compound, papaverine as spasmolytic agent and dihydroergocristine as alpha-blocking agent.

It can be noted that the compounds of the present invention are extremely selective and powerful: for instance the compounds 11 and 12 are 25 and 250 times more active respectively than the comparison compound as to the anti-5 HT activity, whereas they are (25 times less active as regards the adrenolytic activity and 2 times less active as regards the spasmolytic activity.

TABLE

| Compound No. | Uterus of female rat - EC$_{50}$μg/ml | Clones induced by Tryptamine ED$_{50}$mg/kg sc | Seminal vesicle of guinea pig EC$_{50}$μg/ml | Antagonizing activity against toxicity induced by adrenalin in the rat | Ileus of guinea pig BaCl$_2$ EC$_{50}$μg/ml | LD$_{50}$ in the mouse mg/kg iv |
|---|---|---|---|---|---|---|
| 2 | 0.005 | 10 | 1.5 | >0.320 | 10 | 22.5 |
| 5 | 0.003 | 0.51 | 0.2 | >0.320 | 7.5 | 45 |
| 7 | 0.007 | 2.47 | 0.8 | >0.320 | 5 | 50.2 |
| 9 | 0.005 | 4.25 | 0.1 | >0.320 | 15 | 34.5 |

TABLE-continued

| Compound No. | Uterus of female rat - EC$_{50}$μg/ml | Clones induced by Tryptamine ED$_{50}$mg/kg sc | Seminal vesicle of guinea pig EC$_{50}$μg/ml | Antagonizing activity against toxicity induced by adrenalin in the rat | Ileus of guinea pig BaCl$_2$ EC$_{50}$μg/ml | LD$_{50}$ in the mouse mg/kg iv |
|---|---|---|---|---|---|---|
| 10 | 0.005 | 7.2 | 0.07 | >0.320 | 5 | 51 |
| 11 | 0.0002 | 0.016 | 1 | >0.320 | 15 | 22.3 |
| 12 | 0.00002 | 0.046 | 1 | >0.320 | 15 | 20 |
| Methergoline | 0.005 | 0.062 | — | — | — | 21.2 |
| Dihydroergocristine methansulfonate | — | — | 0.008 | 0.003 | — | 70 |
| Papaverin | — | — | — | — | 8.9 | 38 |

The present invention is better illustrated by the following Examples:

EXAMPLE 1

A 5 g solution of 6-methyl-8β-azidomethylergoline in 120 mls of dimethylformamide (DMF) is supplemented with 0.643 g NaH, at the 80% concentration in mineral oil. The mixture is then heated to 40° C. for one hour until the nitrogen release ceases and, after cooling to 20° C., 3.64 g methyltosylate are added. The mixture is maintained under stirring at room temperature for one hour and then poured into 500 mls of water. The solid precipitate is washed with water, and then crystallized from methanol. 4.1 g of 1,6-dimethyl-8β-azidomethylergoline are obtained, m.p. 168°-9° C., $[\alpha]_D^{20} = -85°$ (c=0.5 C$_5$H$_5$N) M+396.

UV$\lambda_{max}^{MeOH}$ 290 mμ (ε6430); 227 mμ (ε24.900).

The 1,6-dimethyl-8β-azidomethyl-9, 10-didehydroergoline is likewise prepared, m.p. 145°-7° C. (IsOH).

EXAMPLE 2

3.2 g 1,6-dimethyl-8β-azidomethyl-9, 10-didehydroergoline in 150 mls of isopropyl alcohol are treated with 6.4 g NaBH$_4$ and heated to reflux under stirring and under nitrogen atmosphere for 24 hours. After this time further 2 g of NaBH$_4$ are added and the heating is continued for 24 hours more. The reaction mixture is poured into water and extracted with chloroform. The chloroform extract is chromatographed onto SiO$_2$ and the product is eluted with CH$_2$Cl$_2$/MeOH/NH$_4$OH (9/1/0.5). 1.6 g of 1,6-dimethyl-8β-aminomethyl-9, 10-didehydroergoline are thus obtained.

EXAMPLE 3

2 g of 8β-aminomethyl-6-methyl-9, 10-didehydroergoline (T. Fehr et al, Eur. J. Med. Chem. 9, 597, 1974) are dissolved together with 2.1 g of triethylamine in 50 mls of dioxane. This solution is supplemented with 3.76 g of hexahydro-1H-azepinyl-sulfamoylchloride dissolved in 10 mls dioxane. The mixture is heated to 55° C. for 6 hours and then poured on ice and extracted with chloroform. From the chloroform extract a solid residue remains which is crystallized two times from methanol, whereby 2.2 g of 1-(1H-hexahydroazepine)-3-(6-methyl-8β-didehydroergolenyl-methyl) sulfonamide (compound No. 7) are obtained.

The compounds Nos. 1, 3, 5, 9, 11 and 12 are likewise prepared.

EXAMPLE 4

To 1.5 g of 8β-aminomethyl-6-methylergoline (L. Bernardi et al. Gazz. Chim. It. 94, 936, 1964) and 1.60 g of isopropyl-ethylamine, dissolved in 40 mls of dioxane, 2.4 g of pyrrolidin-sulfamoylchloride dissolved in 10 mls of dioxane are added. The mixture, after heating to 75°-80° C. for 2 hours, is poured on ice and extracted with chloroform. The chloroformic extract is chromatographed on SiO$_2$ and the product is eluted with CH$_2$Cl$_2$/MeOH (95/5). After crystallization from methanol, 1.15 g of 1-(6-methyl-8β-ergolenylmethyl)-3-pyrrolidinosulfonamide (compound No. 4) are obtained.

The compounds Nos. 2, 6, 8 and 10 are likewise obtained.

(1) 1,1-dimethyl-3-(6-methyl-8β-didehydroergolenylmethyl)-sulfonamide m.p. 231°-34° C. (MeOH), $[\alpha]_D^{20} +55.5°$ (c=0.5 C$_5$H$_5$N), M+360. UV$\lambda_{MeOH}^{max}$ 311 mμ (ε8950); 243 mμ (ε19.150); 228 mμ (ε20.200). For C$_{18}$H$_{24}$N$_4$O$_2$S calc. % 59.97; H% 6.71; N% 15.54. Found C% 59.78; H% 6.57; N% 15.37.

(2) 1,1-dimethyl-3-(6-methyl-8β-ergolenylmethyl)-sulfonamide m.p. 243-5 (MeOH), $[\alpha]_D^{20} -68$ (c=0.5 C$_5$H$_5$N) M+362. UV$\lambda_{max}^{MeOH}$ 282 mμ (ε7250), 225 mμ (ε27.500). For C$_{18}$H$_{26}$N$_4$O$_2$S calc. C% 59.64; H% 7.23; N% 15.46. Found C% 59.27; H% 7.09; N% 15.44.

(3) 1-(6-methyl-8β-didehydroergolenylmethyl)-3-pyrrolidine-sulfonamide, m.p. 209-211 (MeOH) $[\alpha]_D^{20} +32.4$ (c=0.5 C$_5$H$_5$N) M+386. UV$\lambda_{max}^{MeOH}$ 311 mμ (ε8750); 240 mμ (ε20.500); 226 mμ (ε22.100). For C$_{20}$H$_{26}$N$_4$O$_2$S calc. C% 62.15; H% 6.78; N% 14.50. Found C% 61.28; H% 6.93; N% 14.27.

(4) 1-(6-methyl-8β-ergolenylmethyl)-3-pyrrolidinosulfonamide m.p. 227°-9° (MeOH) $[\alpha]_D^{20} -38$ (c=0.5 C$_5$H$_5$N) M+388. UV$\lambda_{max}^{MeOH}$ 281 mμ (ε4900); 225 mμ (ε28.300). For C$_{20}$H$_{28}$N$_4$O$_2$S calc. C% 61.83; H% 7.26; N% 14.42. Found C% 63.09; H% 7.24; N% 14.52.

(5) 1-(6-methyl-8β-didehydroergolenylmethyl)-3-piperidino-sulfonamide, m.p. 194-6 (EtOAc) $[\alpha]_D^{20} +70°$ (c=0.5 C$_5$H$_5$N), M+400. UV$\lambda_{max}^{MeOH}$ 310 mμ (ε9450); 240 mμ (ε20.500); 228 mμ (ε24.900). For C$_{21}$H$_{28}$N$_4$O$_2$S calc. C% 62.97, H% 7.05, N% 13.99. Found C% 61.76, H% 6.81, N% 13.92.

(6) 1-(6-methyl-8β-ergolenylmethyl)-3-piperidinosulfonamide m.p. 236°-8° (MeOH) $[\alpha]_D^{20} -74$ (c=0.5 C$_5$H$_5$N) M+402. UV$\lambda_{max}^{MeOH}$ 283 mμ (ε6.300), 229 mμ (ε19.200). For C$_{21}$H$_{30}$N$_4$O$_2$S calc. C% 62.65, H% 7.51, N% 13.92. Found C% 62.09, H% 7.26, N% 13.65.

(7) 1-(1H-hexahydroazepine)-3-(6-methyl-8β-didehydroergolenyl-methyl)-sulfonamide, m.p. 207-9 (MeOH) $[\alpha]_D^{20} +37$ (c=0.5 C$_5$H$_5$N) M+414. UV$\lambda_{max}^{MeOH}$ mμ 311 (ε9200), 240 mμ (ε19.750), 228 mμ (ε21.500). For C$_{22}$H$_{30}$N$_4$O$_2$S calc. C% 63.73, H% 7.29, N% 13.51. Found C% 62.27, H% 7.30, N% 13.22.

(8) 1-(1H-hexahydroazepine)3-(6-methyl-8β-ergolenylmethyl)-sulfonamide, m.p. 226-8 (MeOH) $[\alpha]_D^{20} -50$ (c=0.5 C$_5$H$_5$N) M+416. UV$\lambda_{max}^{MeOH}$ 282 mμ (ε7600), 226 mμ (ε29.300). For C$_{22}$H$_{32}$N$_4$O$_2$S calc. C% 63.43, H% 7.74, N% 13.45. Found C% 63.68, H% 7.69, N% 13.52.

(9) 1-(6-methyl-8β-didehydroergolenylmethyl)-3-morpholino-sulfonamide, m.p. 235°–37° (MeOh) $[\alpha]_D^{20}$ +50.6 (c=0.5 C$_5$H$_5$N) M+402. UVλ$_{max}^{MeOH}$ 310 mμ (ε10.000), 240 mμ (ε21.200), 227 mμ (ε23.100). For C$_{20}$H$_{26}$N$_4$O$_3$S calc. C% 59.68, H% 6.51, N% 13.92. Found C% 58.72, H% 6.41, N% 13.65.

(10) 1-(6-methyl-8β-ergolenylmethyl-3-morpholino-sulfonamide m.p. 232°–34° (MeOH) $[\alpha]_D^{20}$ −64° (c=0.5 C$_5$H$_5$N) M+ 404. UVλ$_{max}^{MeOH}$ 282 mμ (ε12.900), 229 mμ (ε34.600). For C$_{20}$H$_{28}$N$_4$O$_3$S calc. C% 5938, H% 6.98, N% 13.85. Found C% 58.24, H% 6.85, N% 13.54.

(11) 1-(1,6-dimethyl-8β-didehydroergolenylmethyl)-3-pyrrolidine-sulfonamide, m.p. 120°–30° (MeOH) $[\alpha]_D^{20}$ +58° (c=0.5 C$_5$H$_5$N) M+400. UVλ$_{max}^{MeOH}$ 326 mμ (ε9050), 248 mμ (ε22.400), 232 mμ (ε24.600). For C$_{21}$H$_{28}$N$_4$O$_2$S calc. % 62.97, H% 7.05, N% 13.99. Found C% 62.43, H% 6.90, N% 13.71.

(12) 1-(1,6-dimethyl-8β-didehydroergolenylmethyl)-3-piperidino-sulfonamide, m.p. 180°–185° (MeOH) $[\alpha]_D^{20}$ +67 M+414. UVλ$_{max}^{MeOH}$ 321 mμ (ε9500) 247 mμ (ε22.200) 231 mμ (ε24.300). For C$_{22}$H$_{30}$N$_4$O$_2$S calc. C% 63.74; H% 7.29; N% 13.52. Found C% 63.10; H% 7.10; N% 13.31.

What we claim is:

1. Sulfamoyl compounds of 8-β-aminoemethylergoline having the formula:

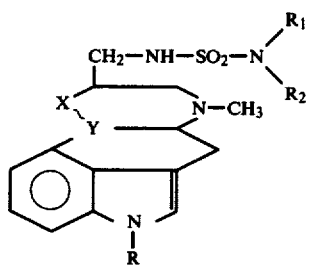

wherein
x~y is CH=C or CH$_2$—CH

R is hydrogen, C$_1$–C$_3$ alkyl, C$_3$–C$_5$ alkenyl or C$_3$–C$_4$ alkyne,

R$_1$=R$_2$=C$_1$–C$_3$ alkyl, or R$_1$ and R$_2$ are connected to each other to form a ring with the adjacent nitrogen atom which ring is the piperazino, piperidino, morpholino, pyrrolidino, or hexahydroazepino group.

2. The compound according to claim 1, which is 1,1-dimethyl-3-(6-methyl-8β-didehydroergolenylmethyl) sulfonamide.

3. The compound according to claim 1, which is 1,1-dimethyl-3-(6-methyl-8β-ergolenylmethyl)-sulfonamide.

4. The compound according to claim 1, which is 1-(6-methyl-8-β-didehydroergolenylmethyl)-3-pyrrolidine-sulfonamide.

5. The compound according to claim 1, in which is 1-(6-methyl-8β-ergolenylmethyl)-3-pyrrolidine-sulfonamide.

6. The compound according to claim 1, which is 1-(6-methyl-8β-didehydroergolenylmethyl)-3-piperidino-sulfonamide.

7. The compound according to claim 1, which is 1-(6-methyl-8β-ergolenylmethyl-3-piperidino-sulfonamide.

8. The compound according to claim 1, which is 1-(1H-hexahydroazepine)-3-(6-methyl-8β-didehydroergolenylmethyl) sulfonamide.

9. The compound according to claim 1, which is 1-(1H-hexahydroazepine)-3-6-methyl-8β-ergolenylmethyl) sulfonamide.

10. The compound according to claim 1 which is 1-(6-methyl-8β-didehydroergolenylmethyl)-3-morpholino sulfonamide.

11. The compound according to claim 1 which is 1-(6-methyl-8β-ergolenylmethyl)-3-morpholino sulfonamide.

12. The compound according to claim 1 which is 1-1,6-dimethyl-8β-didehydroergolenylmethyl)-3-pyrrolidine sulfonamide.

13. The compound according to claim 1 which is 1-(1-6-dimethyl-8β-didehydroergolenylmethyl)-3-piperidino-sulfonamide.

14. Pharmaceutical compositions, useful as antimigrainic, anti-hypertensive and psychopharmaceutically active drugs, characterized in that they contain, as the active ingredient, a compound according to claim 1 and the pharmaceutically acceptable salts thereof with non toxic, organic or inorganic acids.

15. A method for the preparation of the compounds according to claim 1, characterized in that a compound having formula:

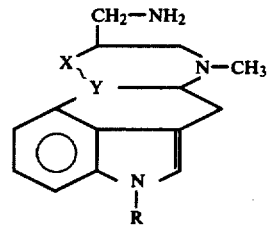

wherein x~y and R have the above meanings is reacted with a compound having formula:

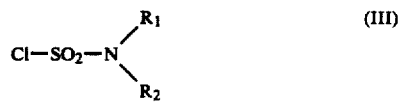

wherein R$_1$ and R$_2$ also have the above defined meanings, the reaction being carried out in an aprotic solvent, such as acetone, tetrahydrofurane, dioxane, dimethylformamide, dimethylsulfoxide, hexamethylenphosphoric triamide, in the presence of an inorganic base, or an organic base at a temperature of between −20° C. and +150° C., the desired reaction product being then isolated.

16. A method according to claim 15 wherein R$_1$ and R$_2$ are C$_1$–C$_3$ alkyl or connected to each other to form a ring.

17. A pharmaceutical composition according to claim 14 wherein R$_1$ and R$_2$ are C$_1$–C$_3$ alkyl or connected to each other to form a ring.

18. A compound according to claim 1 wherein R$_1$ and R$_2$ are C$_1$–C$_3$ alkyl or connected to each other to form a ring having C$_1$–C$_8$ members.